United States Patent
Abenaim et al.

(10) Patent No.: US 9,679,169 B2
(45) Date of Patent: Jun. 13, 2017

(54) SAMPLE CARRIER IDENTIFICATION

(75) Inventors: Daniel Abenaim, Lynnfield, MA (US);
Mark Tverskoy, Andover, MA (US);
Lou Poulo, Andover, MA (US)

(73) Assignee: Analogic Corporation, Peabody, MA (US)

( * ) Notice: Subject to any disclaimer, the term of this patent is extended or adjusted under 35 U.S.C. 154(b) by 390 days.

(21) Appl. No.: 13/697,028

(22) PCT Filed: May 12, 2010

(86) PCT No.: PCT/US2010/034476
§ 371 (c)(1),
(2), (4) Date: Nov. 9, 2012

(87) PCT Pub. No.: WO2011/142749
PCT Pub. Date: Nov. 17, 2011

(65) Prior Publication Data
US 2014/0197925 A1    Jul. 17, 2014

(51) Int. Cl.
*G06K 7/10* (2006.01)
*B01L 3/00* (2006.01)
*G01N 35/00* (2006.01)

(52) U.S. Cl.
CPC ............ *G06K 7/10009* (2013.01); *B01L 3/54* (2013.01); *G01N 35/00732* (2013.01);
(Continued)

(58) Field of Classification Search
None
See application file for complete search history.

(56) References Cited

U.S. PATENT DOCUMENTS 7,911,346 B1 * 3/2011 Claudatos ............ G06Q 10/087
340/572.1
2003/0113906 A1 * 6/2003 Sangha et al. ............. 435/287.2
(Continued)

FOREIGN PATENT DOCUMENTS

DE    WO-02/40708    *    5/2002
JP    2001-147231 A        5/2001
(Continued)

OTHER PUBLICATIONS

Japanese Office Action dated Nov. 5, 2013, Patent App. No. 2013-510058, translation attached.
(Continued)

*Primary Examiner* — Quan-Zhen Wang
*Assistant Examiner* — Chico A Foxx
(74) *Attorney, Agent, or Firm* — Anthony M. Del Zoppo, III; Driggs, Hogg, Daugherty & Del Zoppo Co., LPA

(57) ABSTRACT

A sample carrier (102) includes a sample support region (104) that supports a sample to be processed by a sample carrier processing apparatus and storage and communications circuitry (106) that includes a wireless interface (502) that wirelessly communicates with a storage component reader of the sample processing apparatus when the sample carrier is loaded in the sample processing apparatus for processing. A sample carrier processing apparatus (100) includes a plurality of sample carrier receiving regions (116) respectively configured to receive individual sample carriers carrying samples to be processed by the sample carrier processing apparatus and a plurality of storage component readers (120), one for each of the plurality of sample carrier receiving regions and respectively configured to wirelessly communicate, one to one, with the sample carrier in a corresponding one of the sample carrier receiving regions.

21 Claims, 8 Drawing Sheets

(52) U.S. Cl.
CPC ... *B01L 2200/025* (2013.01); *B01L 2300/022* (2013.01); *B01L 2300/023* (2013.01); *B01L 2300/024* (2013.01); *G01N 2035/00138* (2013.01); *G01N 2035/00841* (2013.01)

(56) References Cited

U.S. PATENT DOCUMENTS

| | | | |
|---|---|---|---|
| 2004/0100415 A1* | 5/2004 | Veitch et al. | 343/850 |
| 2005/0220677 A1* | 10/2005 | Sangha | A61B 10/0051 422/550 |
| 2006/0040341 A1* | 2/2006 | Bland et al. | 435/40.5 |
| 2006/0051239 A1* | 3/2006 | Massaro | 422/63 |
| 2006/0283945 A1* | 12/2006 | Excoffier et al. | 235/439 |
| 2007/0036686 A1* | 2/2007 | Hatamian et al. | 422/102 |
| 2008/0143480 A1* | 6/2008 | Egbert | H04B 5/0062 340/10.1 |
| 2008/0177612 A1* | 7/2008 | Starink et al. | 705/8 |
| 2008/0238627 A1* | 10/2008 | Oldham | H02J 7/0054 340/10.1 |
| 2008/0240983 A1* | 10/2008 | Harris | 422/52 |
| 2010/0025464 A1* | 2/2010 | Trueeb et al. | 235/385 |
| 2010/0167294 A1* | 7/2010 | Huang et al. | 435/6 |
| 2010/0262379 A1* | 10/2010 | Frazier | 702/20 |
| 2014/0240100 A1* | 8/2014 | Johns | G06K 19/0723 340/10.6 |

FOREIGN PATENT DOCUMENTS

| | | |
|---|---|---|
| JP | 2001-272410 A | 10/2001 |
| JP | 2005-309587 | 11/2005 |
| JP | 2008-64586 A | 3/2006 |
| WO | WO-2010/004332 * | 1/2010 |

OTHER PUBLICATIONS

International search report for PCT/US2010/034476 published as WO 2011/142749 A1.
Maxim Integrated Products, Glossary Definition for RFID, 2010, 1 sheet.
Maxim Integrated Products, 1-Wire RFID Alternatives a Contact Based Alternative to RFID, 2010, 2 sheets.
ST, 64 Kbit EEPROM with password protection & dual interface: 400 kHz I2C serial bus & ISO 15693 RF protocol at 13.56 MHz, Manual, Apr. 2010, 126 pages, Doc ID 15170 Rev 9, www.st.com.
TAGSYS RFID, Case Study: An RFID-Based Management Solution for Biobanks, 2010, 2 sheets, www.tagsysrfid.com.

* cited by examiner

SAMPLE CARRIER IDENTIFICATION

RELATED APPLICATION

This application is a national filing of PCT application Serial No. PCT/US2010/034476, filed May 12, 2010, published as WO 2011/142749 A1 on Nov. 17, 2011.

TECHNICAL FIELD

The following generally relates to sample carrier identification and is described herein with particular application to identifying and communicating with individual sample carriers of a plurality of sample carriers loaded in a sample processing apparatus; other applications are also contemplated herein.

BACKGROUND

Sample processors have been configured to concurrently receive a plurality of sample carriers and parallel process the samples carried by the plurality of sample carriers. In one application, the sample carried by a sample carrier is obtained and attached to the sample carrier at the location of collection. For example, the sample carrier can be a swab that is rubbed against an inside wall of a subject's mouth in order to collect a sample that includes cells. After obtaining the sample, the sample carrier is stored in a container, and the container is labeled with indicia used to uniquely identify and distinguish the sample therein from samples on the sample carriers in other containers.

The container with the sample carrier is then taken to another location (e.g., a laboratory) for processing. Where multiple samples are being processed in parallel, the individual sample carriers are removed from their corresponding containers and loaded into respective processing channels of a carrier support. The indicia of the label on the containers are used to map the sample carriers (and hence the samples) to the individual processing channels of the processing apparatus. By way of example, the technologist loading a sample carrier may manually enter (or electronically scan) the indicia of the label into a database or other software executing on a computer and associate the indicia therein with an identifier of the channel in which the corresponding sample carrier is in.

The samples are then processed and the results are read out and/or stored in memory. The sample carriers can then be unloaded and a next set of sample carriers can be loaded for processing. The results of the processing are associated with the individual samples and hence the subjects through the mapping of the label indicia and the channel identifier in the computer. Unfortunately, the above approach is susceptible or prone to human error. By way of example, the technologist may load a sample carrier carrying a sample from John Doe into one channel but inadvertently record in the computer that this sample carrier was loaded into a different channel. As a consequence, the result of the processed sample may be associated with the wrong subject.

SUMMARY

Aspects of the application address the above matters, and others.

In one aspect, a sample carrier includes a sample support region that supports a sample to be processed by a sample carrier processing apparatus and storage and communications circuitry that includes a wireless interface that wirelessly communicates with a storage component reader of the sample processing apparatus when the sample carrier is loaded in the sample processing apparatus for processing.

In another aspect, a sample carrier processing apparatus includes a plurality of sample carrier receiving regions respectively configured to receive individual sample carriers carrying samples to be processed by the sample carrier processing apparatus and a plurality of storage component readers, one for each of the plurality of sample carrier receiving regions and respectively configured to wirelessly communicate, one to one, with the sample carrier in a corresponding one of the sample carrier receiving regions.

In another aspect, a method positioning a plurality of readers over a plurality of sample carriers respectively loaded in a plurality of sample carrier receiving regions of a sample processing apparatus, wherein a single reader is positioned over each of the sample carriers, activating each reader to read a unique identifier of only the sample carrier loaded in a corresponding sample carrier receiving region, mapping, via a controller, the sample carrier unique identifiers respectively the sample carrier receiving regions, processing samples carried by the sample carriers and generating signals indicative of processing results, and associating the signals with respective sample carriers based on the mapping.

In another aspect, a method includes obtaining first identification information from a plurality of sample carriers carrying samples for processing prior to the sample carriers being loaded into a sample processing apparatus, mapping, with a computing device, the first identification information of each of the sample carriers to identification information corresponding to a sample carrier receiving region in which each sample carrier is loaded, processing the samples, obtaining second identification information from the plurality of sample carriers after the sample carries are unloaded from the sample processing apparatus, mapping, with the computing device, the second identification information of each of the sample carriers to the identification information corresponding to the sample carrier receiving region in which each sample carrier is loaded, comparing the first and second identification information, and providing a notification indicative of the comparison.

BRIEF DESCRIPTION OF THE DRAWINGS

The application is illustrated by way of example and not limitation in the figures of the accompanying drawings, in which like references indicate similar elements and in which.

DETAILED DESCRIPTION

Figure 1:
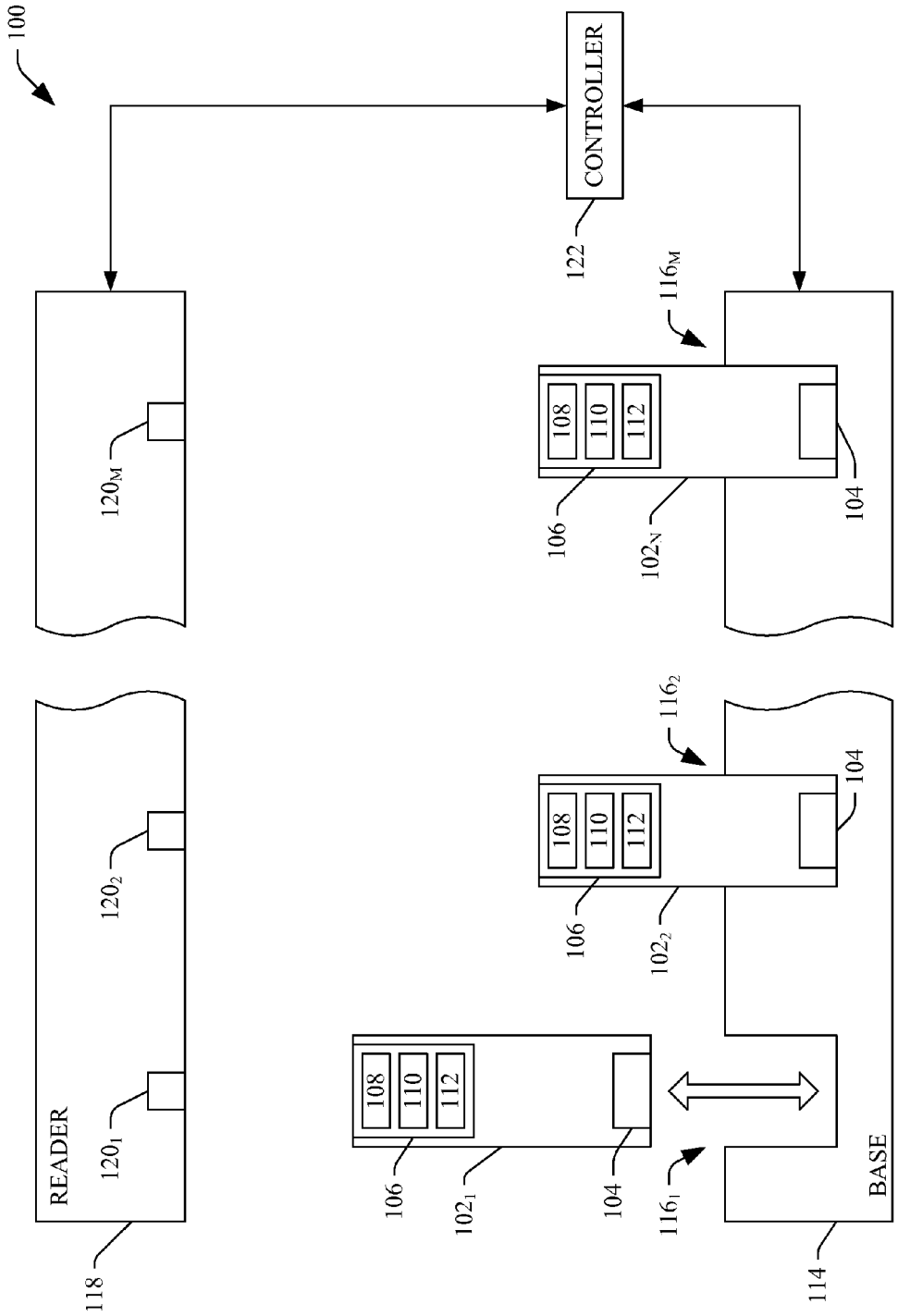
FIGS. 1-3 illustrate an example sample processing apparatus and sample carriers.
Figure 2:
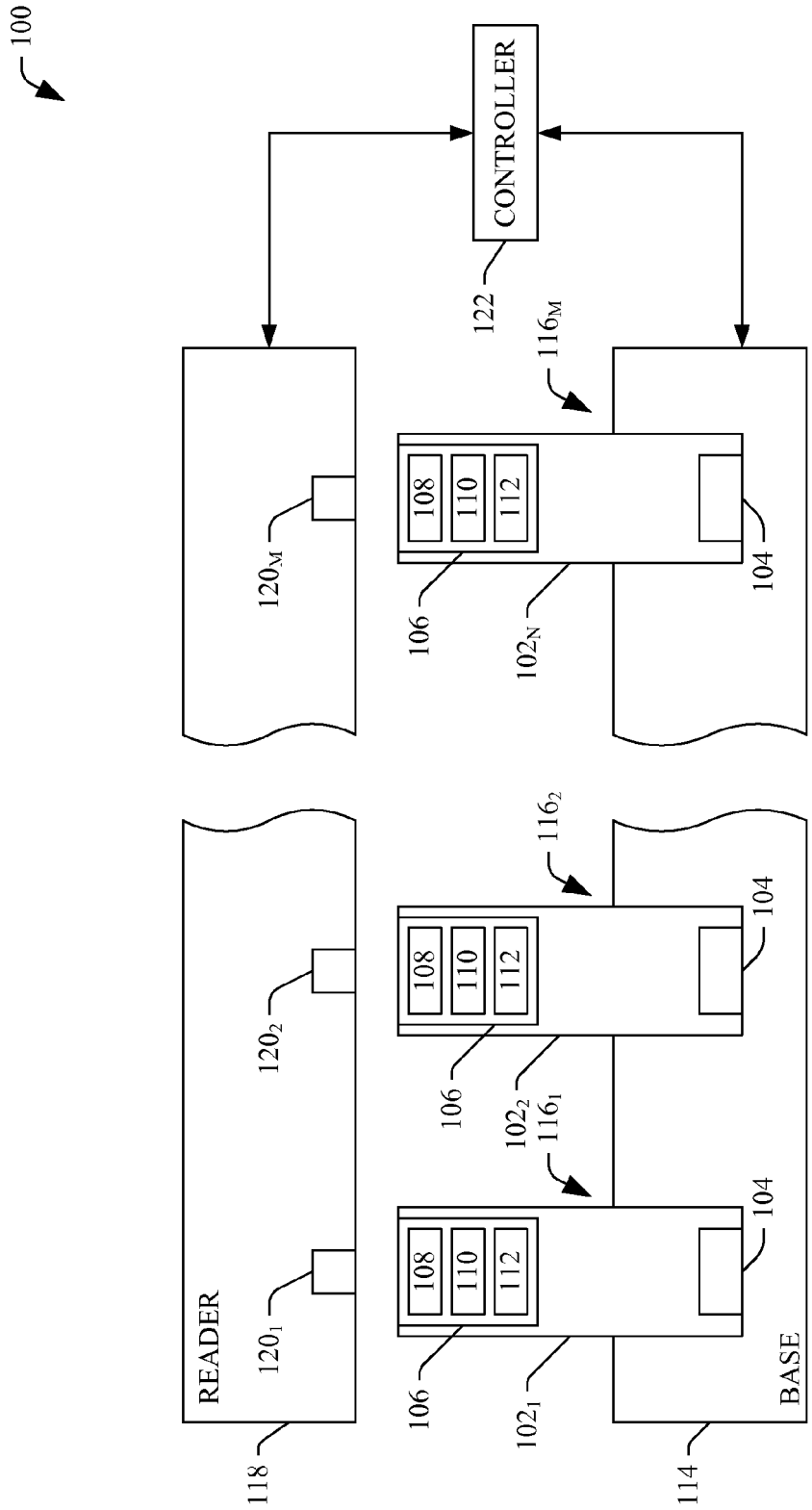
Figure 3:
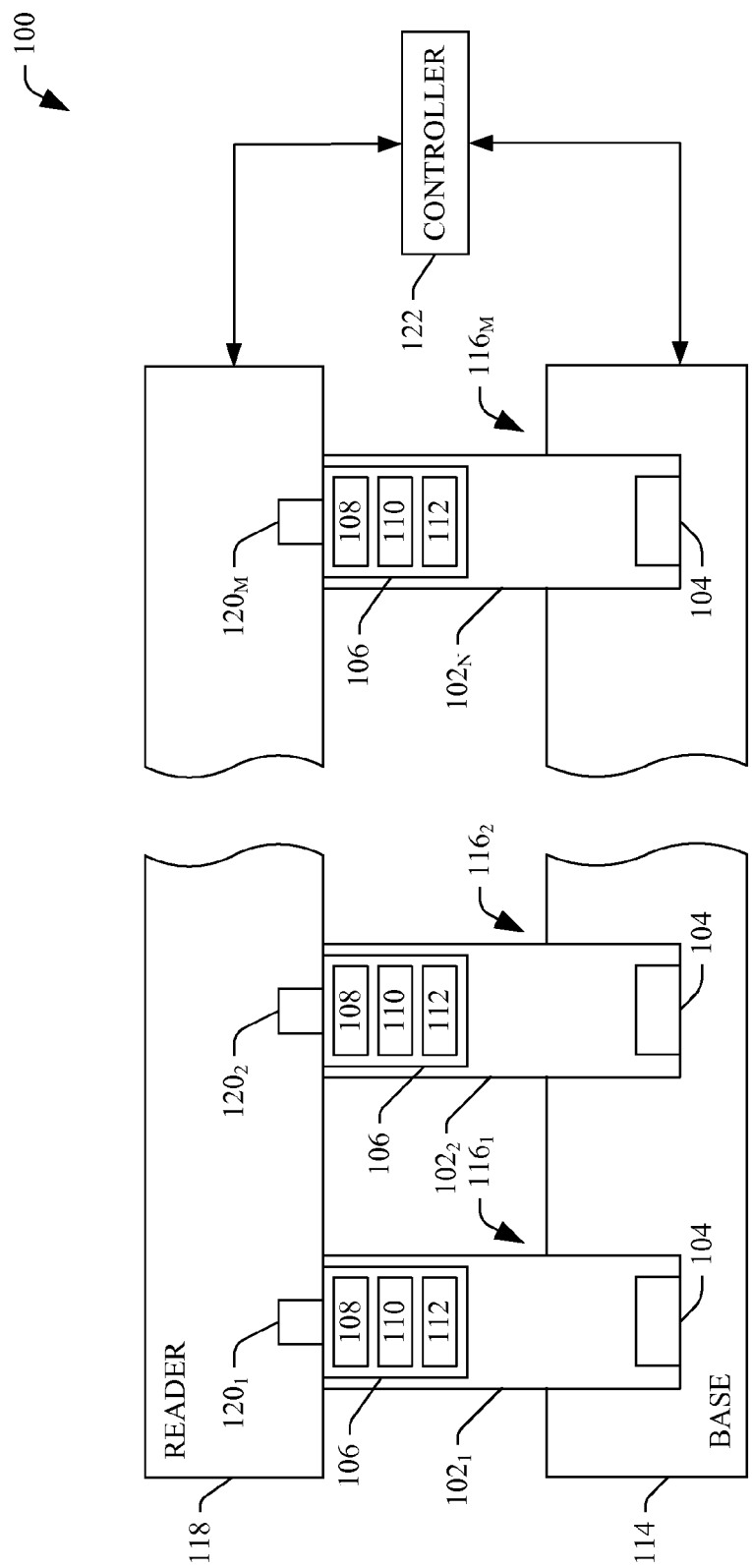

FIGS. 1-3 illustrate an example sample processing apparatus 100 and N sample carriers $102_1$, $102_2$, . . . , $102_N$ (wherein N is an integer equal to or greater than one), collectively referred to herein as sample carriers 102. FIG. 1 shows the sample processing apparatus 100 in a configuration in which sample carriers 102 can be loaded into and/or unloaded from the sample processing apparatus 100. FIGS. 2 and 3 respectively show the sample processing apparatus 100 in a configuration for processing samples of loaded sample carries 102 through wireless and physical contact based interfaces.

The illustrated sample carriers 102 respectively include a sample support region 104 and storage and communications circuitry 106. The sample support region 104 is configured to support a sample to be processed by the sample processing apparatus 100. In one embodiment, the sample support region 104 includes a swab or other material or container for supporting or holding a sample such as blood, saliva, tissue, and/or other sample or specimen of a subject (human or animal). In another embodiment, the sample support region 104 supports other samples (e.g., a paint chip, water, etc.) obtained from other sources for processing.

The storage and communications circuitry 106 includes a communication component 108, logic 110, and a storage component 112. The communication component 108 is configured for interaction with (e.g., receives information from and/or conveys information to) devices remote from the sample carrier 102 such as the sample processing apparatus 100, a suitable electronic based writer, a suitable electronic based reader, and/or other device remote from the sample carrier 102. The logic 110 facilitates controlling such locally, for example, by providing local implementation of the interaction, acting as a slave device of the reader 118. In one instance, the logic 110 may be configured to arbitrate wireless and/or wired access conflicts. The logic 110 also controls writing of information to and/or reading of information from the storage component 112.

The storage component 112 includes memory such as read-only memory, write-once memory, read/write memory, and/or other memory. The particular type of storage element employed may depend on various factors such as a predetermined security level, the type of information to be stored in the storage component 112, and/or other factors. In one embodiment, the storage component 112 at least stores a unique identifier (UID). The UID can be read through the communications component 108 and/or otherwise. The UID allows an authorized user (e.g., a human and/or a computing device) to map a sample carrier 102 (and hence a sample supported thereon) to a particular sample and/or source of the sample. Of course, various other information (e.g., source name, sample type, collector, date, etc.) can also be stored in the storage component 112. In another embodiment, there is no UID stored in the storage component 112.

As described in greater detail below, the communication component 108 includes a wireless (or contactless) communications interface and/or a contact (or wired) communications interface. A wireless interface may provide a sterile, non-contact boundary between the sample carrier 102 and a device communicating with it, and a contact interface may provide a relatively higher level of security, for example, mitigating unauthorized interception of wireless signals. Where the wireless and contact interfaces each have a UID, the UIDs can be set to the same UID or they can be mapped, correlated, or otherwise associated so that either UID can be used to identify and track the sample carrier 102.

Also described in greater detail below, in one embodiment, the storage and communications circuitry 106 can be part of the sample carrier 102. For example, the storage and communications circuitry 106 may be partially or fully embedded in the sample carrier 102, part of the outside of the sample carrier 102, or otherwise part of the storage and communications circuitry 106. This includes being a non-removable part or component of a disposable sample carrier 102 in which the entire sample carrier 102 is contained in one-piece. In this manner, the UID can follow the sample of the sample carrier 102, which may mitigate erroneously associating a UID with a sample carried by different sample carrier 102.

In another embodiment, the storage and communications circuitry 106 may be removable attached to the sample carrier 102. With this embodiment, the storage and communications circuitry 106 may be disposable or re-usable (e.g., after suitable sterilization and re-programming) with another sample carrier 102. Where re-usable, the storage and communications circuitry 106 may be programmable, allowing for another UID to be stored in the storage component 112, replacing the previously stored UID so that the identification stored therein remains unique.

The sample processing apparatus 100 includes a base 114 with M sample carrier receiving regions $116_1$, $116_2$, ..., $116_M$ (wherein M is an integer equal to or greater than one) loaded therein, collectively referred to herein as sample carrier receiving regions 116. In the illustrated embodiment, the N sample carriers 102 are loaded in the M sample carrier receiving regions 116. It is to be appreciated that N can be equal to or less than M.

The sample processing apparatus 100 also includes an interrogator or reader 118 for reading the content of the storage components 112 of the storage and communications circuitry 106 of the sample carriers 102 loaded therein. The reader 118 may or may not be physically part of the base 114. The illustrated reader 118 includes M storage component readers $120_1$, $120_2$, ..., $120_M$ (wherein M is an integer equal to or greater than one), collectively referred to herein as storage component readers 120.

Figure 4A:
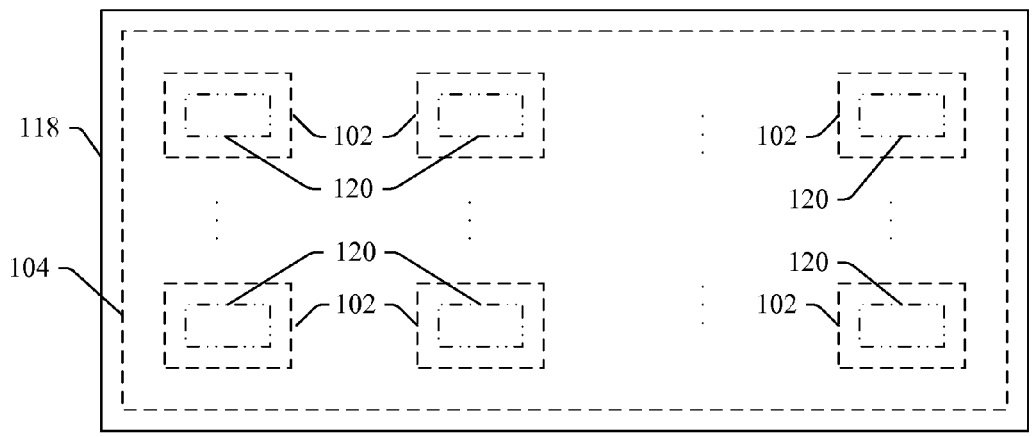
FIGS. 4A, 4B, and 4C illustrate sample carrier readers in connection with sample carriers loaded in the sample processing apparatus.
Figure 4B:
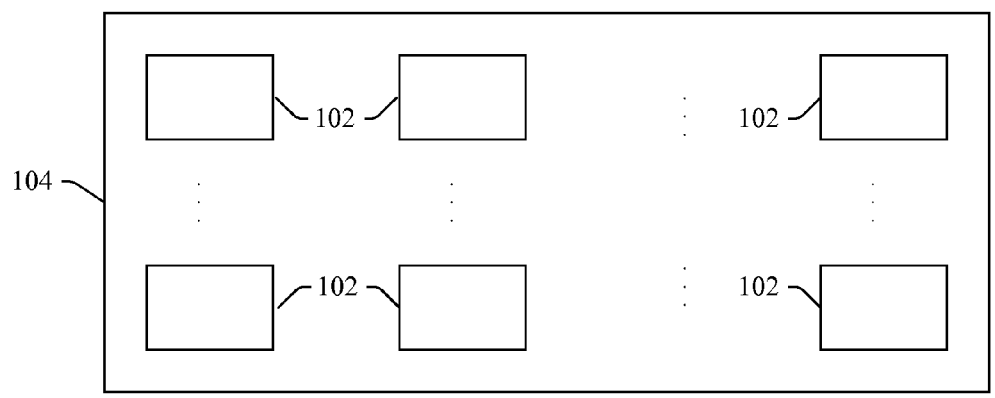
Figure 4C:
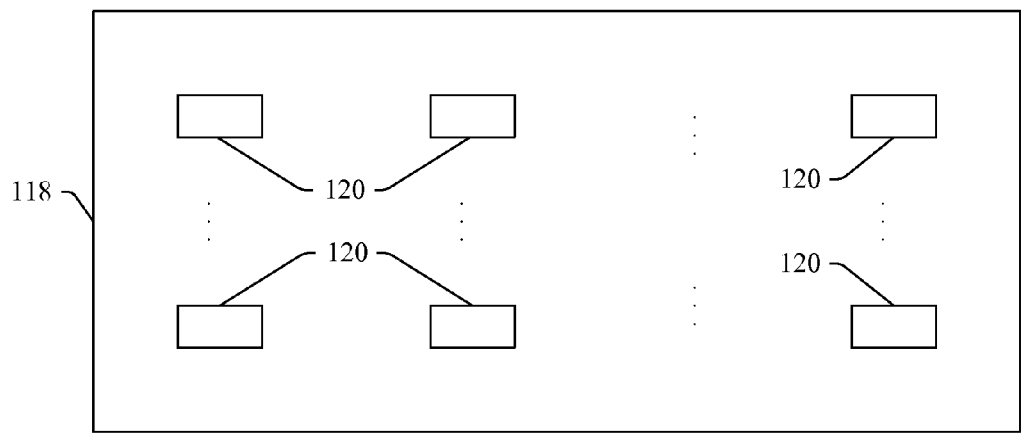

In the illustrated embodiment, the storage component readers 120 are arranged with respect to the reader 118 so that individual storage component readers 120 can be aligned with individual sample carrier receiving regions 116 and hence individual sample carriers 102 loaded therein. This is illustrated in FIG. 4A which shows a top down view with the reader 118 positioned over the base 114 for communication with the storage and communications circuitry 106 of the sample carriers 102 loaded therein. FIGS. 4B and 4C respectively show a top down view of the base 114 with the reader 118 moved away from the base 114 and a bottom up view of the reader 118.

This arrangement allows for one-to-one communication between a storage component reader 120 and a storage and communications circuitry 106 of a sample carrier 102. Such communication may provide for unambiguous reading of a UID and/or other information from the sample carrier 102. For example, such one-to-one communication may mitigate a storage component reader 120 (or other circuitry having to determine or identify which of a plurality of samples carriers 102 the storage component reader 120 is communicating with, if any, at any given time.

Generally, a system designed for one-to-one communication may still encounter cases where the plurality of samples carriers 102 are detected. Mitigations, such as the use a sample carrier's signal strength, may be used to distinguish which one of the multiple detected carriers 102, if any, is in the expected slot. A well-designed system for one-to-one communication can be expected to have very good discrimination between desired and undesired sample carriers 102, so that the one-to-one premise can be achieved in practice.

Where no sample carrier 102 is in a sample carrier receiving region 116, the corresponding storage component reader 120 does not communicate with storage and communications circuitry 106 of a sample carrier 102. Furthermore, in other embodiments, two or more sample carriers 102 communicate with a single storage component reader 120, a single sample carrier 102 communicates with two or more storage component readers 120, and two or more sample carriers 102 communicate with two or more storage component readers 120.

Returning to FIGS. 1-3, a controller 122 controls the base 114 and/or the reader 120, and/or one or more components thereof. The controller 122 may have and/or can communicate with memory storing one or more computer readable and executable instructions and executes such instructions.

It is to be understood that the geometry (e.g., the shape, size, etc.) of the components discussed herein is provided for explanatory purposes and is not limiting. In other embodiments, other geometries are contemplated. Furthermore, the location of the storage and communications circuitry 106 and sample support region 104 may be otherwise located with respect to the sample carrier 102.

Figure 5:
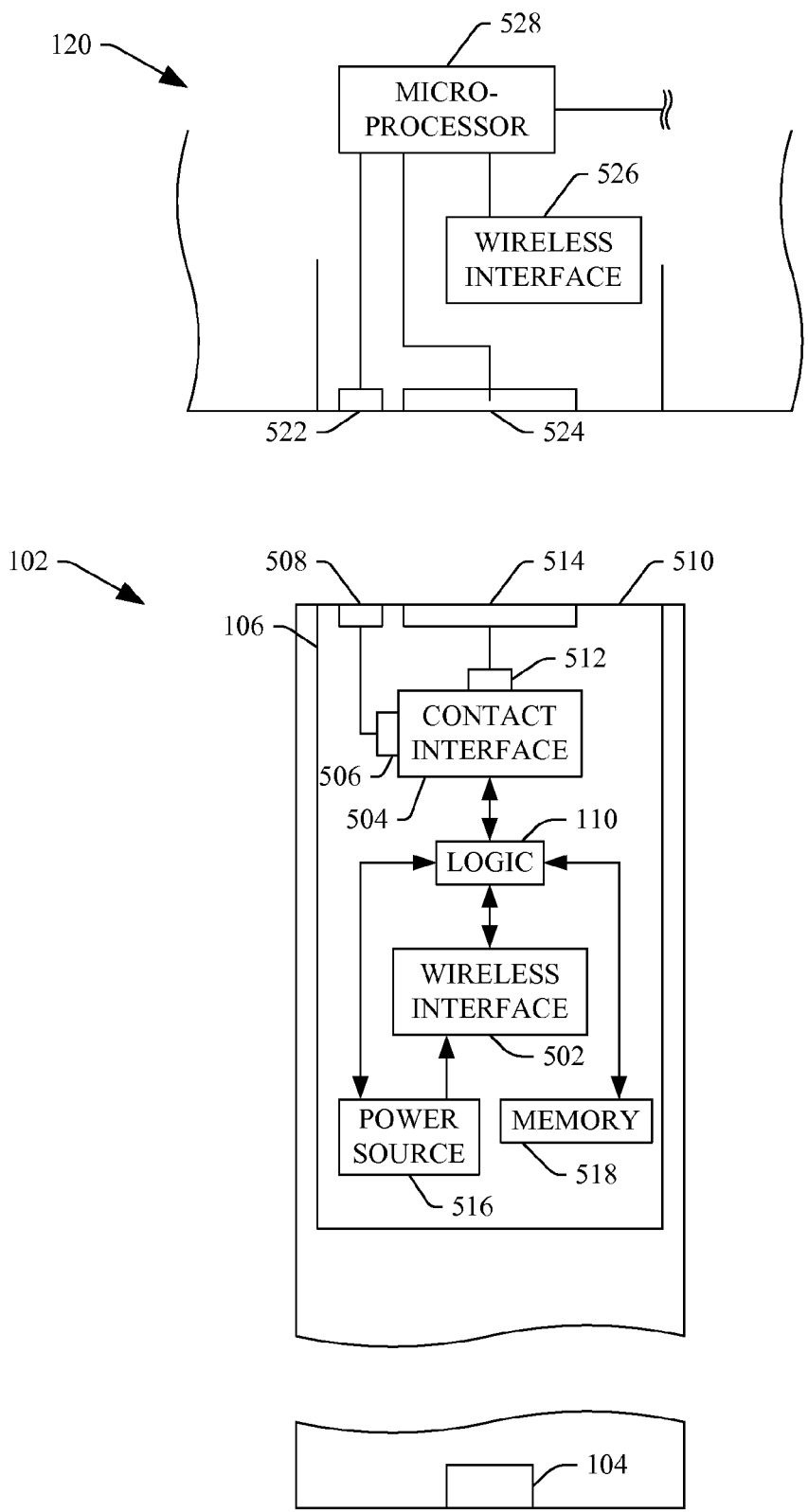
FIG. 5 illustrates an example sample carrier with wireless and contact interfaces.

FIG. 5 illustrates an example sample carrier 102 in which the storage and communications circuitry 106 includes an integrated chip with both a wireless interface 502 and a contact interface 504 and a reader 120 configured to communicate with the wireless interface and contact interfaces 502 and 504.

The illustrated wireless interface 502 includes a radio frequency identification (RFID) interface and the illustrated contact interface 504 includes an I²C (Inter-Integrated Circuit) interface. A non-limiting example of such storage and communications circuitry 106 includes the 64 Kbit EEPROM (part number M24LR64-R), a product of STMicroelectronics of Geneva, Switzerland. In other embodiments, other wireless and/or contact interfaces may be employed.

The wireless interface 502 includes an antenna such as a coil, a wire, or other transducer that can transmit and/or receive electromagnetic waves. The contact interface 504 includes a first electrically conductive contact 506 in electrical communication with a first electrically conductive region 508 of an outer surface 510 of the sample carrier 102, and a second electrically conductive contact 512 in electrical communication with a second electrically conductive region 514 of the outer surface 510 of the sample carrier 102. In some embodiments, there may be other and/or additional electrical contacts.

The electrically conductive regions 508 and 514 are arranged so that physical contact can be made therewith when the sample carrier 102 is loaded in the base 114 of the sample processing apparatus 100. The contact 506, the region 508, and an electrical path therebetween are electrically separated (or isolated) from the contact 512, the region 514, and an electrical path therebetween.

Figure 6:
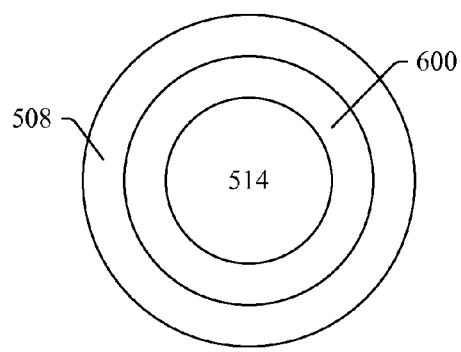
FIG. 6 illustrates example contact interface.

Various approaches can be employed to electrically separate the electrically conductive regions 508 and 514. By way of example, FIG. 6 illustrates an example embodiment in which the first and second electrically conductive region 508 and 514 are configured as concentric circles separated by an electrical insulator 600. Other configurations are also contemplated herein. Any of a variety of mechanical means may be used to ensure proper alignment of contacts between each sample 102 and the corresponding reader 120.

Returning to FIG. 5 the logic 110 includes instructions for operating the storage and communications circuitry 106 in various modes such as wireless mode, contact mode, and/or other modes. The optional power source 516 supplies power for the logic 110 for designs that do not derive power from the querying RF signal (e.g., with passive RFID devices) or via the contacts. Memory 518 stores various computer readable and executable instructions for the logic 110. The memory 518 may or may not be part of the storage component 112.

In another embodiment, the contact interface 504 includes a 1-Wire® device, which is a product of Dallas Semiconductor Corporation of Dallas Tex., or other contact interface. In another embodiment, the storage component 112 includes only the wireless interface 502 or only the contact interface 504. In another embodiment, the storage component 112 includes more than one wireless interface 502 and/or more than one contact interface 504. In another embodiment, the wireless communication between the reader 118 and the sample carrier 102 is achieved through capacitive or other coupling.

The storage component reader 120 includes complementary interfaces, including contact interfaces 522 and 524 a wireless interface 526. Other storage component readers 120 may have additional contact and/or wireless interfaces. A micro-processor 528 controls the interfaces and interacts with the controller 122 (FIGS. 1-3).

Figure 7:
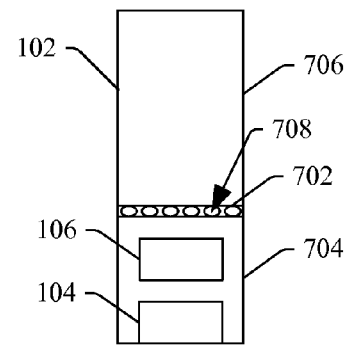
FIGS. 7, 8, and 9 illustrate example sample carriers configured to be broken into a more compact sample carrier.
Figure 8:
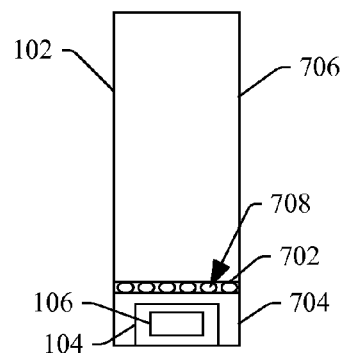
Figure 9:
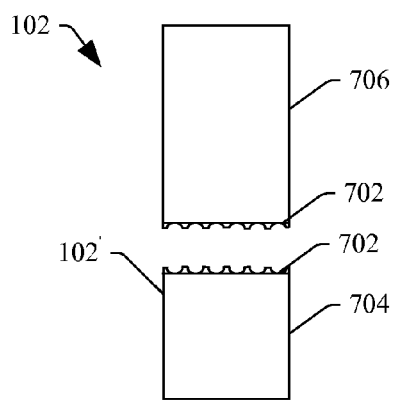

FIGS. 7, 8, and 9 illustrate example embodiments of the sample carrier 102.

With these embodiments, the sample carrier 102 is configured so that it can be readily snapped or broken along a disconnection region or path 702 to divide the sample carrier 102 into two separate regions or pieces 704 and 706, the piece 704 including the sample support region 104 and the storage and communications circuitry 106. The illustrated path 704 includes a plurality of material free regions 708. Additionally or alternatively, a thickness of the material along the path 702 may be relatively thinner than a thickness of the material elsewhere in the sample carrier 102. Other approaches may additionally or alternatively be used to form the disconnection path 702.

With this embodiment, the sample carrier 102 can be of sufficient length to facilitate carrying, applying a sample to, transferring, and/or loading a sample carrier 102 into the sample carrier processing apparatus 100. Then upon loading the sample carrier 102 in the sample carrier processing apparatus 100, the sample carrier 102 can be snapped along the path 702, rendering a compact sample carrier 102 and minimizing the volume of space occupied in the sample carrier processing apparatus 100. With respect to FIG. 7, the storage and communications circuitry 106 is located next to the sample support region 104 in the piece 704. With respect to FIG. 8, the storage and communications circuitry 106 is located at least partially within the sample support region 104. FIG. 9 shows the sample carrier 102 split into the two separate pieces 704 and 706.

Figure 10:
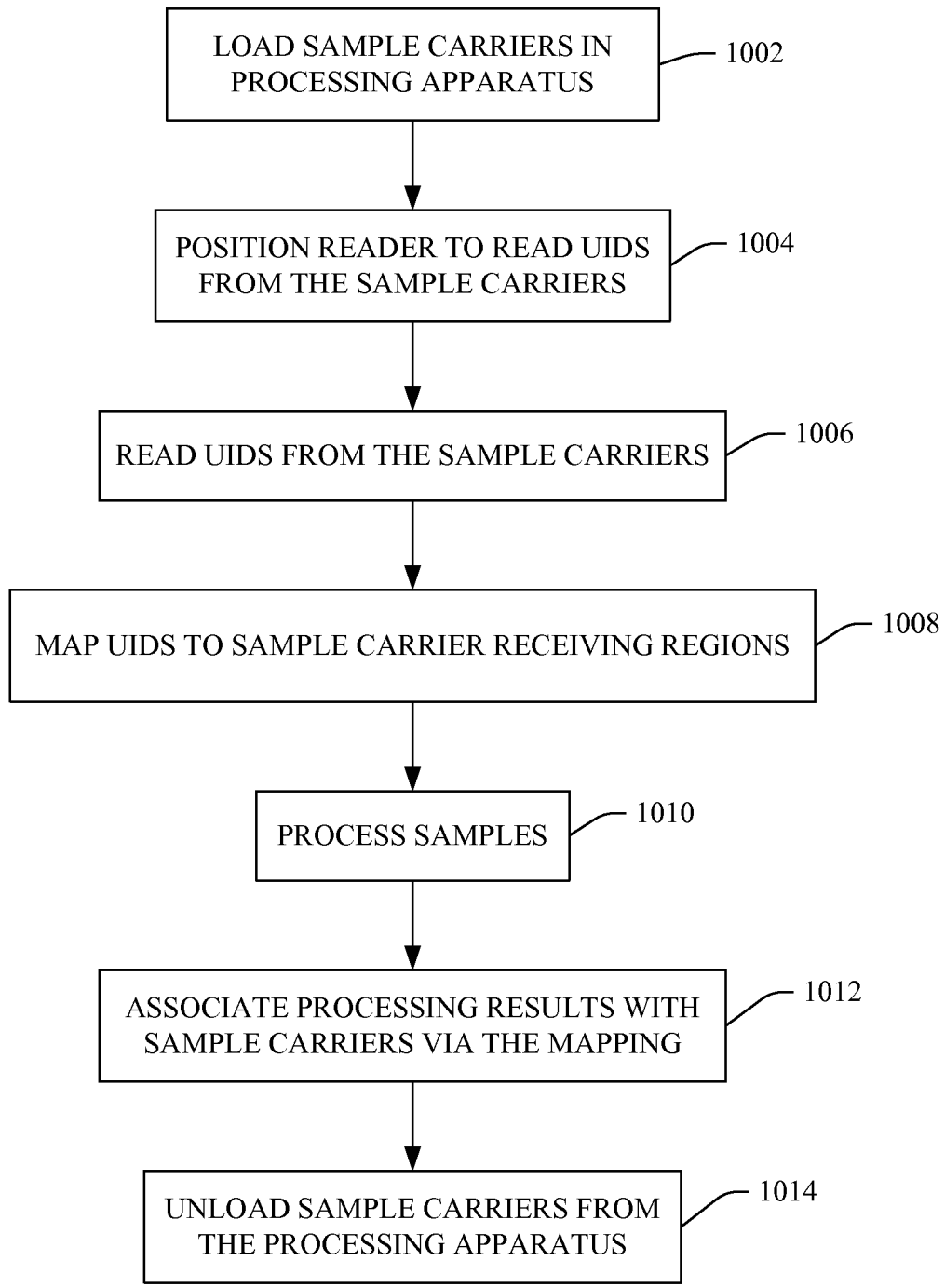
FIGS. 10 and 11 illustrate example methods.

FIG. 10 illustrates a method.

At 1002, a plurality of sample carriers 102 are loaded into respective sample carrier receiving regions 116 of the base 114 of the sample processing apparatus 100. The sample carriers 102 can be randomly or arbitrarily loaded into the sample carrier receiving regions 116. Of course, the sample carriers 102 can also be loaded into designated and/or recorded sample carrier receiving regions 116.

At 1004, the reader 118 is positioned over the sample carrier receiving regions 116.

At 1006, the individual storage component readers 120 of the reader 118 respectively communicate with corresponding ones of the sample carries 102 via the storage and communications circuitry 106 and read the UIDs.

As discussed herein, such communication can be through the wireless and/or contact interfaces 502 and 504 of the sample carrier 102. In one instance, the particular interface employed depends on the configuration of the sample processing apparatus 100. By way of example, where a sample processing apparatus 100 does not support wireless communication, the contact interface 504 is utilized.

In another instance, the two interfaces 502 and 504 provide alternative interfaces, for example, when the sample processing apparatus 100 is unable to communicate over one of the interfaces 502 and 504. In one embodiment, the sample processing apparatus 100 determines which of the interfaces 502 or 504 to utilize for communication. In another embodiment, the particular interface is selected by a user, a default configuration, and/or otherwise.

At 1008, the controller 122 creates a mapping between the UIDs of the sample carriers 102 and the identifications of the sample carrier receiving regions 114 in which the sample carriers 102 are loaded. The controller 122 can store the mapping in local and/or remote memory.

At 1010, the samples are processed by the sample carrier processing apparatus 100.

At 1012, the results of the processing are electronically associated with the sample carriers 102 via the mappings between the UIDs and the sample carrier receiving regions 116.

At 1014, the plurality of sample carriers 102 are unloaded from the sample processing apparatus 100. A next set of sample carriers 102 can be loaded for processing.

Figure 11:
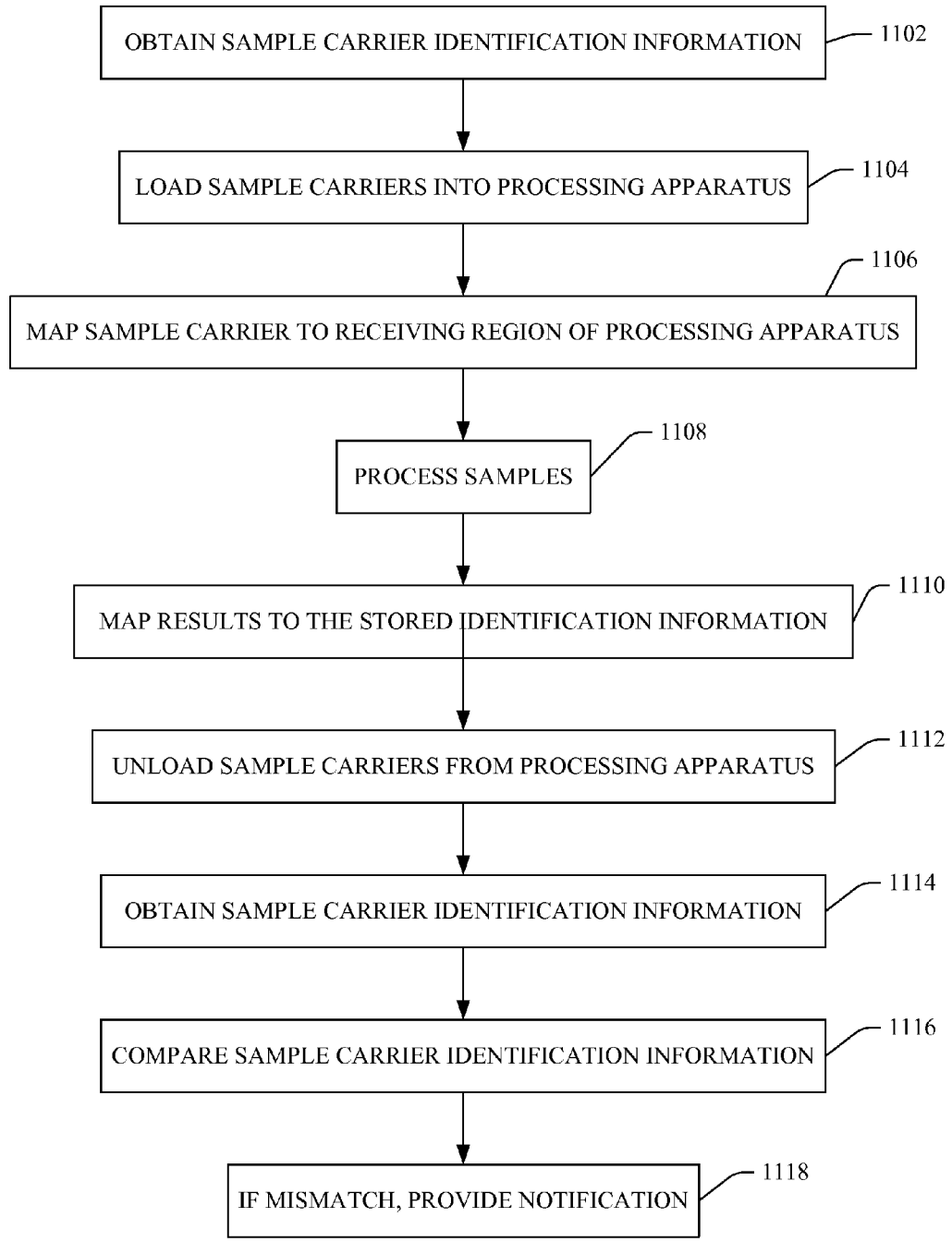

FIG. 11 illustrates another method.

At 1102, identification information of a sample carrier 102 carrying a sample for processing is obtained. As described herein, the identification information can be obtained, using an appropriate electronic reading device, by reading an electronic label of the sample carrier and/or of a container carrying the sample carrier. In yet another instance, the identification information is manually read from such a label by personnel. The identification information is stored in a computing system.

At 1104, the sample carrier 102 is loaded into one of sample carrier support regions 104 of the processing apparatus 100 along with a plurality of other sample carriers 102.

At 1106, the identification information of each sample carrier 102 and identification of the corresponding sample carrier support region 104 are associated or mapped to each other in the computing system.

At 1108, the samples are processed.

At 1110, the processing results are mapped to identification information in the computing system.

At 1112, the sample carriers 102 are removed or unloaded from the processing apparatus 100.

At 1114, the identification information of the sample carriers is again obtained from the label on the sample carrier 102 and/or sample carrier container.

At 1116, the identification information obtained in act 1114 is compared, via the computing system, to the identification information mapped to the processing results, and a signal indicative of the comparison is generated.

If the signal indicates that the identification information does not match each other, then at 1118 the computing system provides a notification, warning, alarm, message, and/or the like to apprise personnel. The information can be provided through visual and/or audio techniques.

Otherwise, the processing results and identification information are printed to hard copy, stored electronically, further processed, conveyed to another apparatus, etc. Generally, a match confirms that the processed sample carrier is the desired sample carrier. Optionally, a notification indicating a match can be provided.

This method may facilitate ensuring the results are associated with the correct identification information. For example, sample carrier A may be placed in channel 1 and sample carrier B may be place in channel 2, but the operator may record (in the computing system) that sample carrier A was placed in channel 2 and sample carrier B was placed in channel 1. In this case, the error in data entry will be caught in acts 1116 and 1118.

This method can also be used in instances in which the reader 120 and/or the storage and communication circuitry 106 (FIG. 1) are not functioning properly so that the information stored in the storage and communication circuitry 106 cannot be correctly obtained. This method can also be used with a sample carrier processing apparatus 100 that does not support communication with the storage and communication circuitry 106. This method can also be used when the sample carrier label is located where the reader 120 is unable to read the label.

The sample carrier processing apparatus 100 discussed herein can be configured to process a plurality of different kinds of samples. Where the sample carrier 102 is a bio-chip, a lab on a chip, or the like carrying a sample with DNA, the sample carrier processing apparatus 100 may be configured to sequence the DNA and/or otherwise process the sample.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A sample carrier, comprising:
   a sample support region that supports a sample of a subject to be processed by a sample processing apparatus;
   storage and communications circuitry that includes a wireless interface that wirelessly communicates with a storage component reader of the sample processing apparatus when the sample carrier is loaded in the sample processing apparatus for processing, wherein the storage and communications circuitry stores a unique identification of the sample carrier and subject information about the subject, and the storage and communications circuitry wirelessly communicates at least the unique identification via the wireless interface to the storage component reader;
   a disconnection region connecting first and second regions of the sample carrier, wherein all of the sample support region and the storage and communications circuitry are located in the same one of the first or second regions, which disconnects from the other of the first or second regions via the disconnection region to form a smaller sample carrier with both the sample support region and the storage and communications circuitry;
   wherein the storage and communications circuitry is programmable, and the unique identification is programmed in the storage and communications circuitry;
   wherein the sample processing apparatus comprises a plurality of storage component readers that include the storage component reader, so when the sample carrier along with a plurality of other sample carriers are loaded into the sample processing apparatus, each storage component reader of the plurality of storage component readers are respectively configured for one to one communication with a respective sample carrier, with respect to the sample carrier and the plurality of other sample carriers, by positioning the storage component reader adjacently over the respective sample carrier, so that the sample carrier and the other plurality of sample carriers only communicate with a respective storage component reader, and wherein the storage and communications circuitry is reprogrammed to remove the unique identification for the sample and add a different unique identification for a subsequent sample.

2. The sample carrier of claim 1, wherein the wireless interface includes a radio frequency identification interface that communicates the unique identification.

3. The sample carrier of claim 1, the storage and communications circuitry, further including:
a contact interface that communicates through a physical electrically conductive path with the storage component readers when the sample carrier is loaded in the sample processing apparatus for processing; and
logic that selects one of the wireless interface or the contact interface for communication with the storage component reader based on a communication from the storage component reader.

4. The sample carrier of claim 3, further including:
a power source which supplies power for the logic.

5. The sample carrier of claim 4, wherein the storage and communications circuitry includes the power source.

6. The sample carrier of claim 3, wherein the storage and communications circuitry includes an integrated chip with both the wireless interface and the contact interface.

7. The sample carrier of claim 1, wherein the sample carrier is a bio-chip.

8. The sample carrier of claim 1, wherein the unique identifier of the sample carrier is read before loading the sample carrier in the sample processing apparatus and associated with a sample carrier receiving region of the sample processing apparatus in which the sample carrier is loaded, the unique identifier of the sample carrier is read again after processing, the said before and after readings of the unique identifier are compared, and a signal is generated based on the comparison and used to confirm that the processed sample carrier is the desired sample carrier.

9. The sample carrier of claim 1, wherein the storage and communications circuitry is located next to the sample support region.

10. The sample carrier of claim 1, wherein the storage and communications circuitry is located at least partially within the sample support region.

11. The sample carrier of claim 1, wherein the wireless interface of the storage and communications circuitry is configured for wirelessly communicate through capacitive coupling.

12. The sample carrier of claim 1, wherein the storage and communications circuitry further comprises logic with includes instructions for operating the storage and communications circuitry and a memory configured to store instructions for the logic.

13. The sample carrier of claim 1, wherein the storage and communications circuitry is only partially embedded in the sample carrier.

14. The sample carrier of claim 1, wherein the storage and communications circuitry is fully embedded in the sample carrier.

15. The sample carrier of claim 1, wherein the storage and communications circuitry is a non-removable part of the sample carrier.

16. The sample carrier of claim 1, wherein the storage and communications circuitry is a removably affixed to the sample carrier.

17. The sample carrier of claim 1, wherein the storage and communications circuitry further stores a sample type of the sample.

18. The sample carrier of claim 1, wherein the storage and communications circuitry further stores a name of a collector of the sample.

19. A method, comprising:
programming a storage and communications circuitry embedded in a sample carrier with a first unique identification;
positioning a plurality of readers over a plurality of sample carriers that each includes a support region that supports a sample and includes an interface for communicating with one of the plurality of readers in a one to one manner, wherein the plurality of sample carriers are respectively loaded in a plurality of sample carrier receiving regions of a sample processing apparatus for processing the sample being supported, wherein each reader of the plurality of readers is singularly positioned adjacently over only one sample carrier of the plurality of sample carriers with respect to a sample carrier receiving region of the plurality of sample carrier receiving regions that receives that sample carrier of the plurality of sample carriers to permit one to one communication therebetween, and the plurality of sample carriers includes the sample carrier with the first unique identification programmed in the embedded storage and communications circuitry and the other sample carriers of the plurality of sample carriers each further include an embedded storage and communications circuitry with a stored unique identification, wherein a plurality of unique identifications that includes the first unique identification and the stored unique identification respectively correspond to a unique identifier for a respective sample carrier of the plurality of sample carriers;
activating each reader to read a unique identifier of only one respective sample carrier of the plurality of sample carriers that is received in a corresponding sample carrier receiving region that receives the only one respective sample carrier, and each sample carrier of the plurality of sample carriers is read only by the reader of the plurality of readers that is positioned adjacently over the corresponding sample carrier receiving region, and each reader includes a different microprocessor which controls a communication interface which reads the unique identifier via respective one to one communication;
mapping, via a controller, the plurality of sample carriers' unique identifiers respectively to the corresponding sample carrier region of the sample carrier receiving regions;
processing the samples carried by the plurality of sample carriers respectively and generating signals indicative of the processing results of each of the plurality of sample carriers while the plurality of sample carriers are positioned in a respective sample carrier region of the plurality of sample carrier receiving regions;
associating the signals respectively with sample carriers of the plurality of sample carriers based on the mapping; and re-programming the storage and communications circuitry with the first unique identification with a different unique identification for subsequent processing of another sample with the sample carrier.

20. The method of claim 19, wherein a reader wirelessly communicates with a corresponding sample carrier.

21. The method of claim 19, wherein the reader communicates with the corresponding sample carrier through a physical electrical contact.

* * * * *